United States Patent
Waisman et al.

(10) Patent No.: US 10,495,490 B2
(45) Date of Patent: Dec. 3, 2019

(54) APPARATUS AND METHOD FOR IMPROVED OPTICAL FIBER TRANSMISSION

(71) Applicant: LUMENIS LTD., Yokneam Ilit (IL)

(72) Inventors: Tal Waisman, Haifa (IL); Arkady Khachaturov, Haifa (IL); Moshe Elazar, Kadima-Tzoran (IL)

(73) Assignee: Lumenis Ltd. (IL)

( * ) Notice: Subject to any disclaimer, the term of this patent is extended or adjusted under 35 U.S.C. 154(b) by 161 days.

(21) Appl. No.: 15/856,240

(22) Filed: Dec. 28, 2017

(65) Prior Publication Data

US 2018/0188080 A1    Jul. 5, 2018

Related U.S. Application Data

(60) Provisional application No. 62/442,032, filed on Jan. 4, 2017, provisional application No. 62/441,478, filed on Jan. 2, 2017.

(51) Int. Cl.

| | | |
|---|---|---|
| *G01D 5/353* | (2006.01) | |
| *A61B 1/07* | (2006.01) | |
| *A61B 18/24* | (2006.01) | |
| *G02B 6/44* | (2006.01) | |
| *G02B 6/02* | (2006.01) | |
| *A61B 1/018* | (2006.01) | |

(Continued)

(52) U.S. Cl.
CPC .......... *G01D 5/35303* (2013.01); *A61B 1/07* (2013.01); *A61B 18/24* (2013.01); *G02B 6/02395* (2013.01); *G02B 6/4416* (2013.01); *A61B 1/018* (2013.01); *A61B 2018/2244* (2013.01); *A61B 2018/2247* (2017.05); *G02B 6/262* (2013.01); *G02B 6/421* (2013.01); *G02B 6/4292* (2013.01)

(58) Field of Classification Search
CPC ............ G01D 5/35303; G02B 6/02395; G02B 6/4416; G02B 6/4292; G02B 6/421; G02B 6/262; A61B 18/24; A61B 1/07; A61B 2018/2247; A61B 2018/2244; A61B 1/018
USPC ...................................................... 250/227.14
See application file for complete search history.

(56) References Cited

U.S. PATENT DOCUMENTS 4,095,101 A    6/1978   Lemelson
4,883,054 A    11/1989  Fuller et al.
(Continued)

OTHER PUBLICATIONS

Search Report—Corresponding European Application No. 17211259, dated May 18, 2018, 2 pages.

*Primary Examiner* — Seung C Sohn
(74) *Attorney, Agent, or Firm* — ISUS Intellectual Property PLLC

(57) ABSTRACT

An optical fiber assembly includes a central optical fiber core having a longitudinal axis surrounded by a cladding layer along the longitudinal axis, a distal end portion and a proximal end portion; it further comprises a layer of a material at least partially surrounding the cladding layer; the layer of material may be light-sensitive; and, at least two electrodes may be embedded at least partially along the longitudinal axis within the layer of light-sensitive material. The light-sensitive material may be a photoresist material, and the photoresist material characteristics change proportional to the amount of light impinging on the photoresist material. These characteristics may include one or more of electrical resistance changes or voltage changes.

17 Claims, 7 Drawing Sheets

(51) Int. Cl.
      *A61B 18/22*       (2006.01)
      *G02B 6/42*       (2006.01)
      *G02B 6/26*       (2006.01)

(56) References Cited

U.S. PATENT DOCUMENTS

| | | | |
|---|---|---|---|
| 5,104,391 A * | 4/1992 | Ingle | A61B 18/20 250/227.15 |
| 2003/0198447 A1 * | 10/2003 | Kim | G02F 1/3558 385/123 |

\* cited by examiner

APPARATUS AND METHOD FOR IMPROVED OPTICAL FIBER TRANSMISSION

RELATED APPLICATIONS

This application is related to and claims priority to U.S. Provisional Application No. 62/441,478, filed Jan. 2, 2017 and U.S. Provisional Application No. 62/442,032, filed Jan. 4, 2017, both of which applications are herein incorporated by reference in their entireties.

FIELD OF THE PRESENT INVENTION

This invention relates to optical fiber integrity and discloses an apparatus and method for detecting leakage in optical fibers and waveguides of any kind. This invention also relates to an optical connector mechanism for adjusting a waveguide or optical fiber to a medical laser source. Both aspects of the present invention improve optical transmission of optical energy.

BACKGROUND OF THE PRESENT INVENTION

A. Detection of Leakage in Optical Fibers and Waveguide

Waveguides and optical fibers deliver optical energy from one point to another. In the medical field, optical energy is used for both diagnostic and therapeutic purposes. Waveguides and optical fibers are used to transmit optical energy from a source outside the body to a targeted area inside the body. In some procedures, such as laparoscopy, rigid scopes and optical delivery systems may be used; however, often there is a need for flexible optical fibers and guides to reach various organs and body cavities that may be less than ideally positioned, such as, by way of example, the kidneys.

A bent waveguide or optical fiber may lose its integrity or its light guiding capability when it is bent to access the desired body cavity or organ, thus risking exposure to adjacent exposed instruments or body parts as a result of optical leakage. The high-energy levels experienced with certain therapeutic treatments further increase the risk of injury to non-targeted tissue within the body.

Therefore, there is a need for an apparatus and method to accurately monitor optical leakage from a waveguide to increase the safety of laser treatments.

B. Optical Mating of Laser Sources to Different-Sized Optical Fibers and Waveguides Coupling a waveguide to a medical laser source may involve adjustment of different parameters in order to safely and efficiently deliver a laser beam produced by a laser system to the distal end of the waveguide. Often, with medical solid state or gas lasers, a laser beam produced in a laser cavity runs in free space to a fiber port. At the fiber port, an optical fiber may be connected to the laser system through a variety of available optical connectors.

Typically, a medical laser system has a laser cavity which is configured to produce a laser beam which is delivered in free space to a fiber. At such fiber port, the laser beam is characterized, among other things, by a certain spot size, beam quality and power. The fiber port is configured to align a proximal end of an optical fiber to the laser beam. The laser beam then travels through the optical fiber to its distal end towards the targeted tissue. An efficient fiber port should be designed to minimize any deterioration in the beam quality and energy loss. In addition, in order to avoid energy leakage in the optical coupling area and along the optical fiber, the beam should be preferably designed to match the numerical aperture (NA) of the optical fiber. The fiber port may include a focal lens which is configured to focus an incident laser beam into the core section of the optical fiber.

In order to deliver a laser beam having a diameter d into an optical fiber having a diameter D, a fiber port is designed so as to focus the laser beam so that the laser beam diameter is smaller than the fiber diameter (d>D). The greater the difference between the laser beam diameter d and optical fiber diameter D, the greater becomes the acceptable tolerance of mechanical misalignment between the laser beam and optical fiber at the point of coupling. However, the ability of a focal lens at a fiber port to reduce the spot size of a laser beam is limited and is a function, among other things, of the original laser beam diameter, its divergence as it travels through free space and beam quality.

In order to deliver a laser beam into a small diameter fiber such as, for example, 230µ, prior art systems provide a tapered proximal-end fiber 630 as seen in FIG. 6. The tapered proximal-end fiber 630 includes a tapered section 631 and a parallel section 632. Each section has core areas 610 and 620 and clad areas 611 and 621, respectively. Fiber 630 has a main longitudinal axis A-A, and tapered section 631 defines an angle $\alpha$ relative to axis A-A. In this non-limiting example, tapered section 631 has a proximal end, having a diameter D1, facing a fiber port and a distal section having a diameter D2 which is coupled to an optical fiber section 632. A tapered section having, for example, D1 at about 365µ, is capable to deliver an incident laser beam, as characterized in prior art systems, into a 230µ fiber.

As can be seen, an exemplary incident ray R which enters tapered section 631 hits clad area 611 at an angle $\alpha$ and is reflected at the same angle. However, as a general rule, each time reflected ray R hits clad area 611 its relative angle is doubled. According to this example, after reflecting twice after impinging on clad area 611, the reflected ray R enters the parallel section 632 of the optical fiber having an angle of $4\alpha$ relative to the clad area 621. According to this example, as long as the critical angle for total internal reflection inside parallel section 632 is greater than $4\alpha$, ray R may efficiently propagate down the optical fiber. As a general rule, the ray angle relative to the clad section is doubled each time the ray hits the clad area in tapered section 631. Therefore, the numerical aperture (NA) of section 632 limits the number of times a ray can hit the clad in tapered area 631 and still propagate down the optical fiber without leaking.

Once the accumulated angle, due to multiple reflections along tapered section 631 reaches and exceeds the critical angle for total internal reflection of the fiber section 632, energy will leak from the fiber. In other words, the NA of optical fiber 32 limits the acceptable length of tapered section 631 and its maximal proximal diameter D1. One option to deal with this to allow a greater number of rays to safely be propagated along section 632 without leaking is to increase the NA of the fiber. This requires more expensive fibers such as sapphire, germanium or crystal silica and this added expense poses a serious problem when the fiber is a single use, disposable fiber. However, even by using expensive fibers, beam rays having incident angles greater than the critical angle of a better fiber will eventually leak and risk causing harm to the patient and to any adjacent equipment. Therefore, in order to safely deliver a laser beam having a bigger spot size or a higher divergence, the prior art solution described above is insufficient. It is one of the aspects of the current invention to provide an improved optical fiber adaptor.

SUMMARY OF THE PRESENT INVENTION

In an aspect, an optical fiber assembly includes a central optical fiber core having a longitudinal axis surrounded by a cladding layer along the longitudinal axis, a distal end portion and a proximal end portion; it further comprises a layer of a material at least partially surrounding the cladding layer; the layer of material may be light-sensitive; and, at least two electrodes may be embedded at least partially along the longitudinal axis within the layer of light-sensitive material. The light-sensitive material may be a photoresist material, and the photoresist material characteristics change proportional to the amount of light impinging on the photoresist material. These characteristics may include one or more of electrical resistance changes or voltage changes.

In another aspect, the optical fiber assembly may include a console, the console including a laser source for producing laser light energy, and wherein the proximal end portion of the optical fiber assembly is received in the laser source.

In a further aspect, the console may include a programmable controller, and wherein the controller is configured to activate the laser source, whereby activation of the laser source causes laser light energy to flow from the laser source to the proximal end portion of the central optical fiber core through to and out the distal end portion.

In yet another aspect, in the optical fiber assembly, at least two electrodes may be operatively connected to the console; the console may further include circuitry for imposing a voltage potential across the at least two electrodes, and wherein the console further comprises circuitry to detect a change in the voltage potential imposed and forward the detected change to the controller.

In yet a further aspect, the at least two electrodes may be one of: mechanically or electronically connected to the console. Further, any laser light energy which passes through the cladding layer is received in the photoresist material and sensed by the at least two electrodes, the sensing causing a change in the imposed voltage potential across the at least two electrodes.

In an aspect, in the optical fiber assembly, the controller may be configured to receive the change in the imposed potential voltage detected by the detect circuitry, the controller providing one or more of a visual, auditory, numerical or graphical indication to a user of the change in imposed voltage potential on a user interface on the console. A change in potential due to light energy leakage may be caused by bending of the optical fiber core beyond a critical radius of curvature of the optical fiber core. Further, the controller may provide one or more of a visual or numerical indication of bending beyond the critical radius.

In a certain aspect, there is disclosed a method of detecting leakage of an optical fiber assembly. The optical fiber assembly may include a central optical fiber core having a longitudinal axis surrounded by a cladding layer along the longitudinal axis, a distal end portion and a proximal end portion; the assembly may further include a layer of a material at least partially surrounding the cladding layer; the layer of material may be light-sensitive; and, at least two electrodes may be embedded at least partially along the longitudinal axis within the layer of light-sensitive material, and a laser source for producing laser energy. The method may include: providing a voltage potential bias across the at least two electrodes; providing a reading of the voltage potential bias in the absence of the laser source producing laser energy; activating the laser source; detecting a change in voltage potential bias across the at least two electrodes when the laser source is activated, whereby the change in voltage potential is a function of leakage of laser light energy through the cladding layer to the layer of light-sensitive material. The light-sensitive material may be or may include a photoresist.

In another aspect, a change in voltage potential due to light energy leakage may be caused by bending of the optical fiber core beyond a critical radius of curvature of the optical fiber core.

In yet another aspect, the optical fiber assembly may further include a temperature sensor mounted on the distal end portion of the optical fiber assembly. The temperature sensor may be operatively connected to one or more of the at least two electrodes, whereby changes in the temperature sensed by the temperature sensor are transmitted to the console for display of the sensed temperature on the console.

DETAILED DESCRIPTION OF THE PRESENT INVENTION

A. Detection of Leakage

Figure 1:
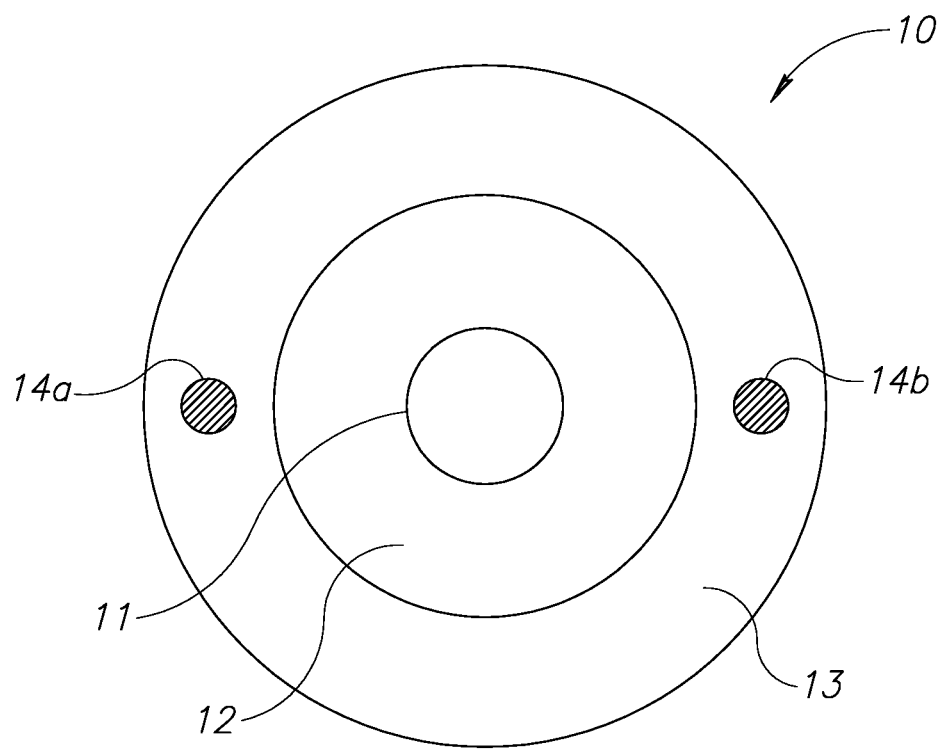
FIG. 1 illustrates one aspect of the present invention of an optical fiber modified to detect leakage of laser light.

One aspect of the invention in which a cross section of an optical fiber 10 in accordance with the present invention is shown in FIG. 1. Optical fiber 10 consists of a core section 11 surrounded by a cladding section 12. A third layer 13 of photoresist material covers the clad section 12. At least two elongated electrodes 14a and 14b are embedded within the photoresist layer 13. The at least two electrodes 14a and 14b are configured to measure electrical characteristics of the photoresist material layer 13 such as electrical impedance, capacitance and/or conductivity.

Figure 2:
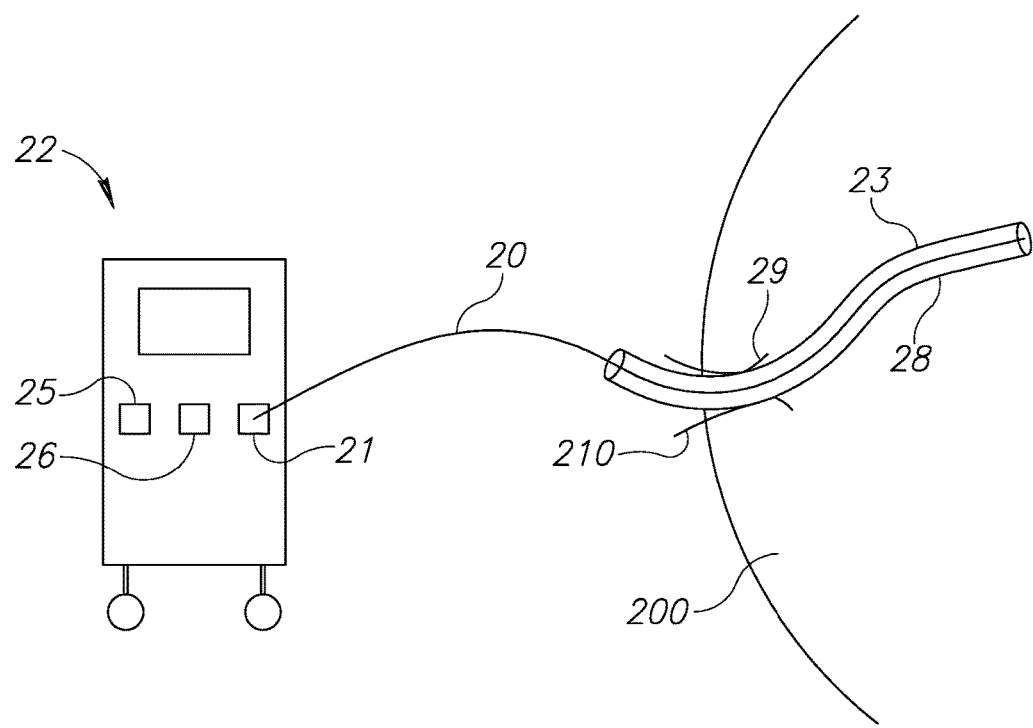
FIG. 2 illustrates an arrangement of the optical fiber of FIG. 1 within a laser delivery system.

During operation, as shown in FIG. 2, the proximal end of fiber 20 is connected to an external laser source/console 22 via connector 21, while the distal portion of fiber 20 is inserted into a human or other body 200 through a natural or artificial opening 210 into a body using a flexible endoscope 23. Laser source/console 22 may include a programmable controller unit 26 with a user interface which controls, among other things, the operation of laser source 22, as well as a unit 25 which is configured to measure electrical signals from the at least two electrodes 14a and 14b. Unit 25 may be configured to establish and maintain a certain voltage between electrodes 14a and 14b in order to detect resistance or conductivity changes in layer 13 by way of voltage changes between the electrodes. Any such voltage changes then are "read" by the unit 25.

According to one embodiment of the invention, electrodes 14a and 14b may have a direct electrical connection with unit 25 through dedicated channels in connector 21. According to another embodiment, connector 21 may be configured to optically couple fiber 20 with laser system 22 while the operation and "reading" of electrodes 14a and 14b may be accomplished wirelessly, as known to those skilled in the art, through a pair of transponders (and shown) located respectively in laser system 22 and on the proximal end of fiber 20.

During a medical procedure, endoscope 23 may be introduced into body 200. Once positioned, other medical instruments, such as a waveguide 20, may be inserted through the endoscope's working channels to a target site. The flexible endoscope, and then any flexible instrument introduced by the endoscope, is constrained to follow the curves within the patient's anatomy or certain obstacles in the path. As shown in FIG. 2 curves 28 and 29 exemplify the typical flexibility that may be required by any instrument which is introduced through the endoscope. As mentioned above, waveguides are vulnerable to optical energy leakage when negotiating such curves. The waveguide may be characterized by a minimum radius R which establishes the limit of the waveguide to continue transmitting the optical energy efficiently and safely. Curvatures having a radius less than R may lead to an optical leakage at or near the point of curvature.

According to an aspect of the invention, laser system 22 may consist of a treatment laser and an aiming laser. In those procedures in which the treatment laser is in the visible spectrum, the same visible laser may serve as a treatment laser in a first irradiating regime and as an aiming laser in a second irradiating regime. In those procedures in which the treatment laser is invisible, laser system 22 may include a second, visible aiming laser source which is introduced into the main optical axis of the treatment laser so that a targeted tissue may be accurately treated by the treatment laser. Targeting a tissue with a visible, non-treatment laser enables better control and safety for the physician providing the treatment.

Turning again to FIG. 1, according to an aspect of the present invention, photoresist layer 13 may be characterized by a first level of electrical resistance as measured by electrodes 14a and 14b in a position in which no optical leakage occurs along waveguide 10. In the event of an optical leakage, which may occur either from core portion 11 or clad portion 12, into photoresist layer 13, electrical resistance as measured by electrodes 14a and 14b will change and in fact may drop and thus conductivity will increase. Therefore, such a resistance drop (or conductivity rise) across electrodes 14a and 14b will be "read" by unit 25 and thus provide an indication of the existence of optical leakage and the amount thereof along waveguide 10.

During the phase of installing a waveguide into an endoscope, according to one aspect of the invention, an aiming laser may be activated and system unit 25 configured to monitor for any electrical changes of photoresist layer 13 to provide an indication of a leakage in the fiber carrying the aiming beam. Controller 26 is configured to provide an indication to a user that waveguide 10 is overly-curved, that is, a curvature along the path in which the curvature radius is smaller than a predefined threshold, discussed above as radius R. The predefined threshold radius R may be selected manually by the user, based on the waveguide in use or it may be selected automatically by laser system 22 based on information received from one or more transponder units (not shown) positioned in the fiber. While any aiming beam leakage likely poses no risk to the scope or body organ, it does provide an indication that the same position along the fiber or waveguide may optically leak during the activation of the treatment laser.

During the laser treatment itself, the treatment laser may be operated intermittently while axial and side forces are applied on scope 23 or waveguide 10 caused by the operator moving these mechanisms. These forces may further bend the scope and the waveguide in certain areas into radiuses smaller than R, which may in turn result in optical leakage. Therefore, according to another aspect of the invention, during treatment, controller 26 may be configured to be provided an electrical signal from module 25 indicating a degree of optical leakage and, based on such signal, the controller 26 may notify the operator by some type of visual or other signal on a user interface (such as a screen or a warning light/alarm) and may even shut down the treatment beam in order to protect the scope and the patient. The operator may then replace the optical fiber in use or take some other action.

According to another embodiment of the invention and in reference to FIG. 1, photoresist layer 13 may be part of a jacketing layer which covers waveguide 10. Electrodes 14a and 14b may be embedded in such photoresist jacket and are configured to read changes in the electrical characteristics of the jacket due to optical leakage from the fiber.

Figure 4A:
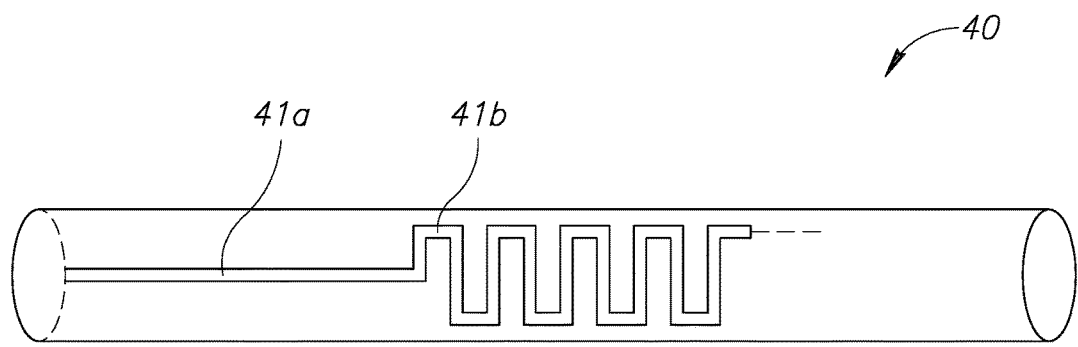
FIGS. 4a, 4b and 5 illustrate further embodiments of the optical fiber of FIG. 1.
Figure 4B:
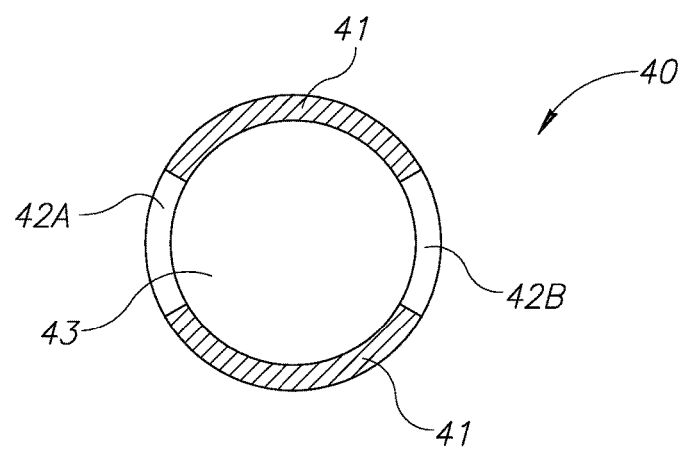

According to another embodiment and referring now to FIGS. 4a and 4b, optical waveguide 40 is shown. FIGS. 4a and 4b show side and cross-sectional views of waveguide 40. According to this embodiment, photoresist material 41 is deposited along waveguide 40 in a pattern such as, for example, linearly as indicated in numeral 41a, or in a zig-zag form as indicated in numeral 41b (or in other forms), on opposite sides of waveguide 40. These opposite patterns 41 shown in FIG. 4b divide the circumference of waveguide 40 into two separate areas. Areas 42A and 42B are areas on which electrodes are deposited, for example, by vacuum evaporation. Since the substrate material 43 is an electrical isolator, according to this embodiment, electrical conductivity/resistance between the first electrode 42A and the second electrode 42B is a function of the electrical characteristics of pattern 41. Changes in the electrical characteristics of photoresist material in pattern 41, as read by electrodes 42, may provide an indication for an optical leakage along waveguide 40. As mentioned above, optical leakage may occur at specific over-curved spots or leakage may occur for other reasons, such as faulty construction of the optical fiber, the waveguide, or the cladding material, even when there is no over-curvature. The comb-like structure shown as 41b increases the light sensing ability area per length unit of fiber 40 and therefore increases the sensitivity of the photoresist so that smaller leakages may be detected.

Figure 3:
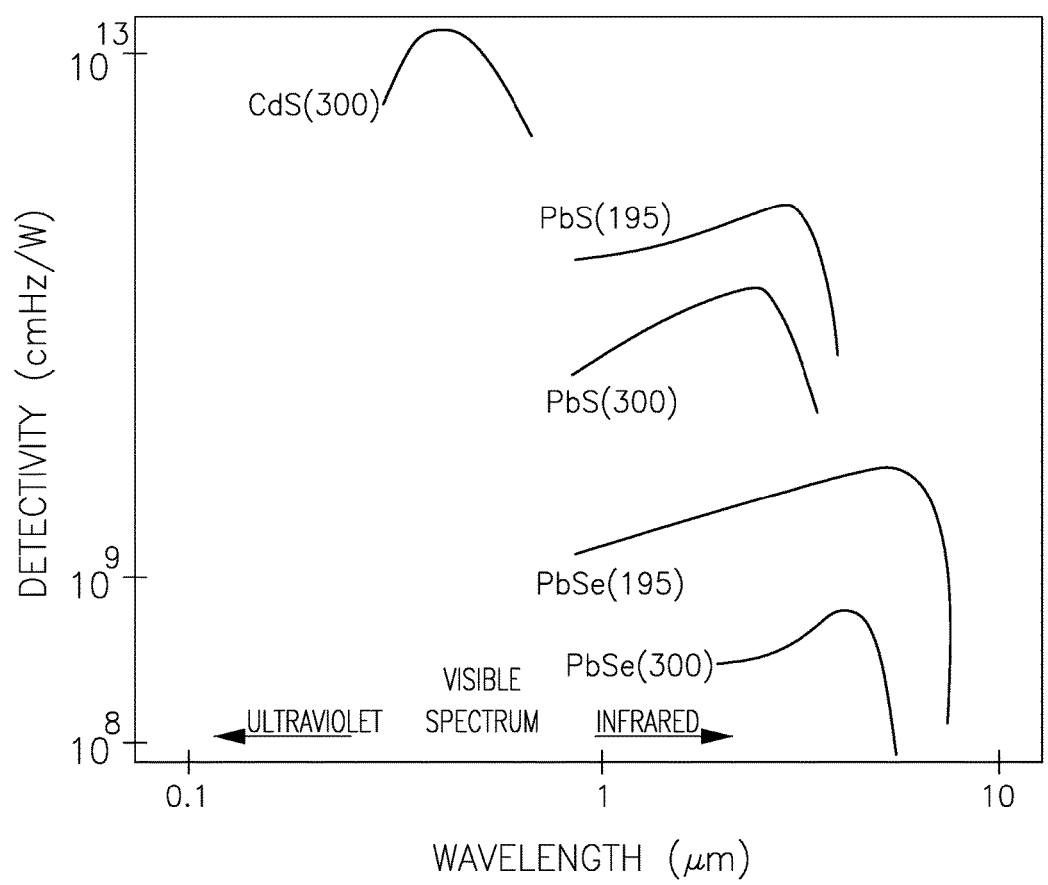
FIG. 3 illustrates a graph showing the spectral response curve of a number of photoresist material used in connection with the optical fiber of FIG. 1.

Referring now to FIG. 3, the photoresist materials used in accordance with the present invention, may be intrinsic or extrinsic, such as lead sulfide, lead selenide, indium antimonide, cadmium sulfide or cadmium selenide. The spectral response curves for each material is different. For example, the spectral response curve of cadmium sulfide matches that of the human eye having a peak sensitivity wavelength of about 560-600 nm in the visible part of the spectrum. Therefore, depositing cadmium sulfide as a photoresist material according to an embodiment of the invention may be used for detecting optical leakage of an aiming beam. However, lead-based photo resist material may be used for the detection of IR invisible lasers.

According to another embodiment, waveguide 40 may be covered partially with two pairs of electrodes 42A and 42B, as in FIG. 4b but also with a second pair of electrodes (not shown). A first pair of electrodes may be configured to read the electrical characteristic of a first pattern of photoresist and a second pair of electrodes is configured to read the electrical characteristic of a second pattern of photoresist. According to this aspect, the first pattern and the second pattern of photoresist may include the same material or different materials. For example, the first pattern of photoresist material may be more sensitive to a first laser and a second pattern of photoresist material may be more sensitive to a second laser. According to one example, the first laser may be an aiming beam and a second laser may be a treatment laser, such as a Neodymium, Thulium, Erbium, Holmium, CO2 or a diode laser. According to another example, the first laser may be a first treatment laser and the second laser may be a second treatment laser. The first and second treatment lasers may have different wavelengths. The first and second treatment lasers however, may have the same wavelength but may differ from one from another by other parameters such as, for example, their energy profile, fluence, pulse duration, repetition rate or peak power.

Figure 5:
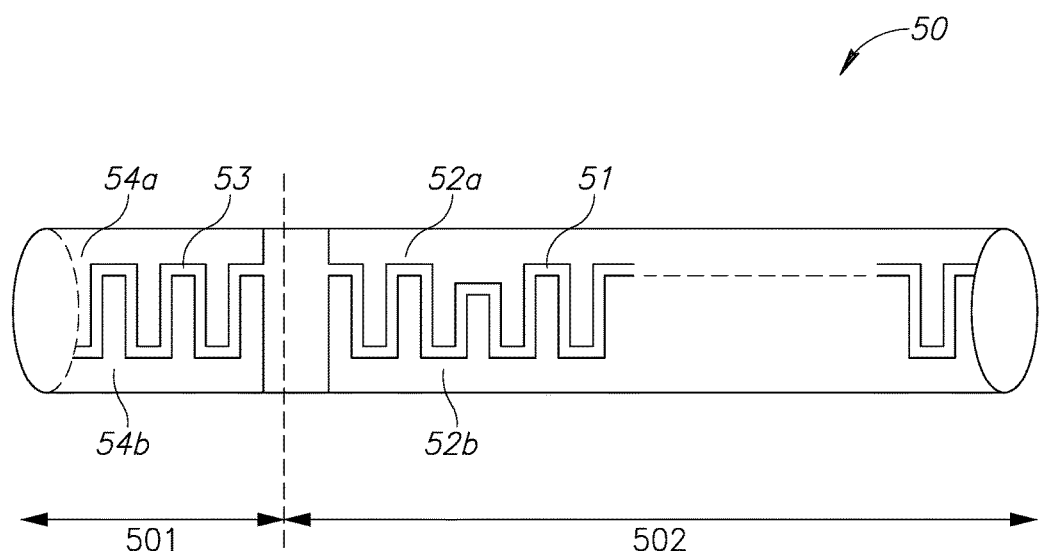

Referring now to FIG. 5, waveguide 50 may be divided into main area 502 and distal area 501. Main area 502 is characterized by at least one photoresist pattern 51 and at least one pair of respective electrodes, a first electrode 52a and a second electrode 52b. Photoresist pattern 51 and electrodes 52a and 52b comprise together a first optical sensor along the waveguide. As mentioned above, more than one optical sensor may be deposited or constructed along area 502. A separate optical sensor having at least one photoresist pattern 53 and at least one pair of electrodes 54a and 54b, may be positioned on distal tip 501 of fiber 50.

During operation, at least part of the distal tip 501 of waveguide 50 will normally be positioned beyond the distal end of the endoscope for protection purposes. When exiting the distal end of the endoscope, the distal tip 501 of waveguide 50 may be exposed to light emanating from a visualization instrument. Therefore, according to this aspect of the invention, photoresist pattern 53 is characterized by having a sensitivity to visible light so that electrodes 54a and 54b may be configured to provide a signal to laser system 22 indicating that the tip of waveguide 50 has exited the distal end of the endoscope and further that the treatment laser can be irradiated without risking the damage to the endoscope that could occur if the distal end remained within the endoscope. Any retraction of the waveguide 50 back into the endoscope may be monitored by a separate photosensor (not shown) at its tip. The controller may turn off treatment laser in this situation to protect the endoscope.

Photo resistors are generally known to be sensitive to temperature changes, as shown in FIG. 3. The distal tip of a waveguide tends to increase in temperature during laser treatment due to the high energy of the optical beam transmitted through the waveguide. Therefore, according to another embodiment, photo sensor structure may cover area 502 only while keeping area 501 without any photo sensor structure. According to another embodiment, distal area 501 may be subject to more aggressive articulation by the articulating tip of the endoscope. Therefore, providing a light sensor according to the present invention at the distal area 501 may provide an indication on the fly to a user while manipulating the endoscope for over-curvatures which may lead to optical leakage. This again may be done by detecting aiming beam leakage or a treatment beam leakage.

According to another embodiment of the present invention, pressure sensitive materials and/or temperature sensitive materials may be deposited between a pair or pairs of electrodes so that changes in pressure or temperature along the waveguide may be monitored. Changes in pressure may also provide an indication of r over curvatures which may lead to optical leaks. Changes in temperature may also provide an indication on the fly of an optical leakage.

In addition, a temperature sensor may be mounted on the fiber assembly, such as at or near the distal end of section 501 shown in FIG. 5. Such temperature sensor may provide a measurement and readout of the temperature of the fiber tip section 501 and/or the area surrounding the distal section 501. The temperature sensor, which may be incorporated into electrodes 54a and/or 54b, may use those electrodes to carry the temperature sensed by the sensor through such electrodes 54a, 54b (or 14a and/or 14b in FIG. 1) to the console 22 through connector 21 to be read out on a user interface on the console 22.

B. Optical Mating of Laser Devices

As generally discussed above, there is continuing demand in the medical laser industry to propagate more energy to allow new treatment regimens or to replace multiple laser cavities system with either a single cavity system or at least reduce the number of laser cavities for the sake of simplicity, reliability and/or cost reduction. The assignee of the present invention, Lumenis Ltd of Israel, has commercialized a Holmium Pulse laser system which is capable of providing about 120 W by combining 4 laser cavities into a single optical path, each providing a power of about 30 W. Inventive aspects of this Holmium Pulse system are described in U.S. patent application Ser. No. 14/660,979. The complete disclosure of this application is herein incorporated by reference.

Figure 6:
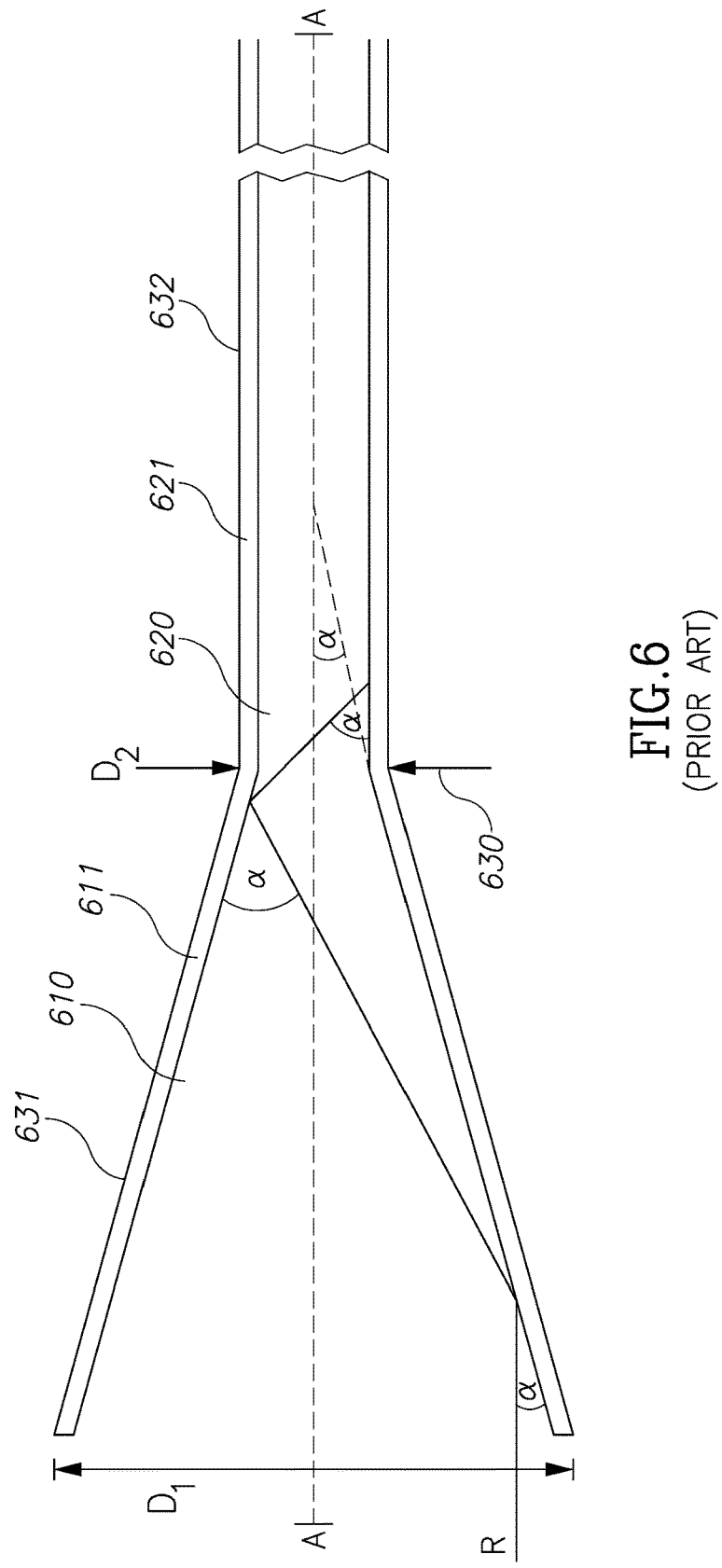
FIG. 6 illustrates a prior art embodiment of another embodiment of the present invention.

A range of optical fibers may be sold with the above-described system, generally having optical fiber diameters from about 200μ up to 600μ. The beam diameter at each laser cavity aperture and its divergence along the propagation in the free space of the system to the fiber port, allow the use of the prior art coupling solution described above with reference to FIG. 6. However, a newly developed system may be configured to produce up to 60 W per cavity. This increase in beam power comes with a lower beam quality, higher divergence and an increased spot size. Under these circumstances, the solution of FIG. 6 may be insufficient to deliver the laser beam efficiently and safely into small diameter fibers.

Figure 7:
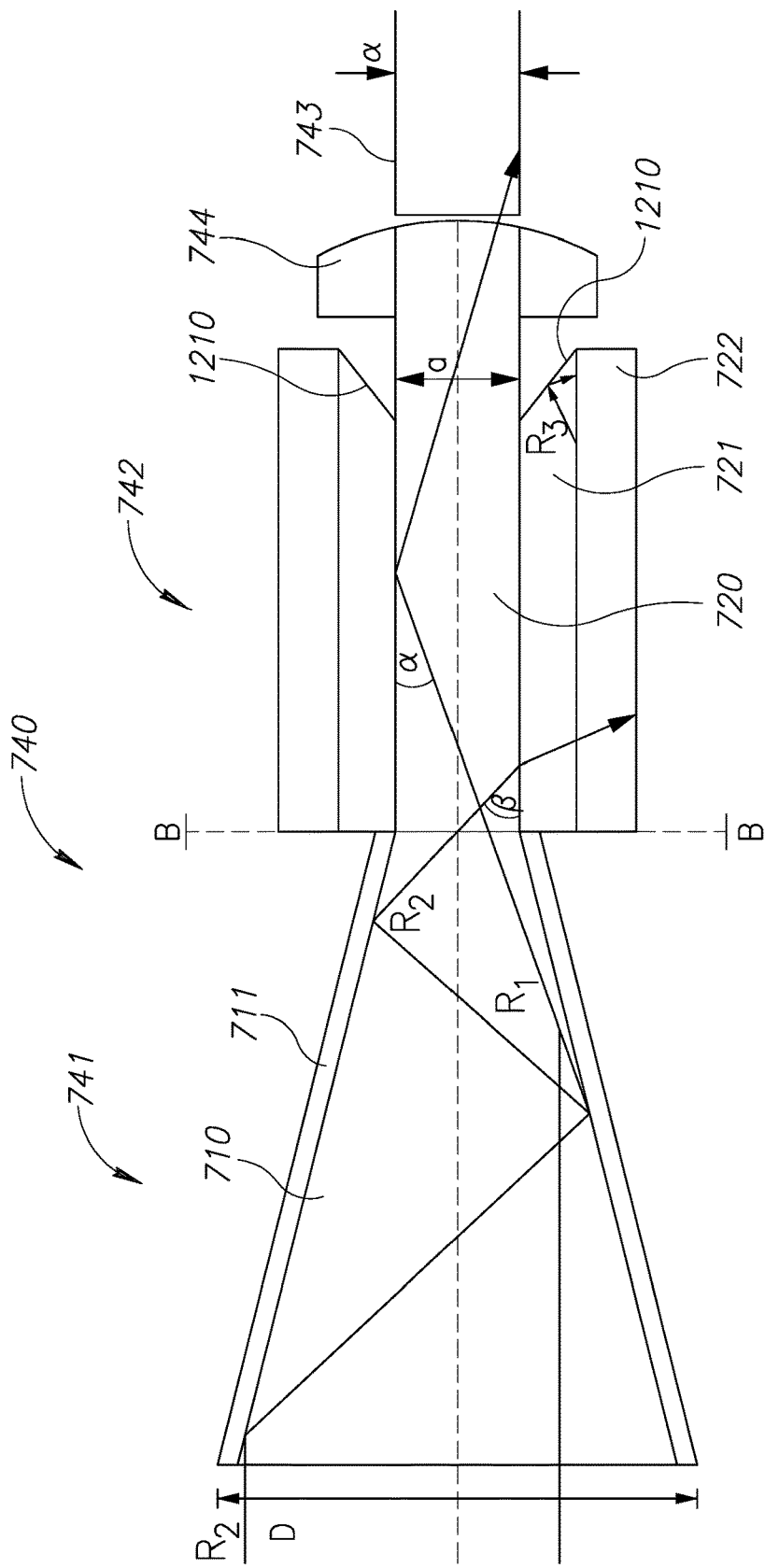
FIG. 7 illustrates an embodiment of as aspect of the present invention.

Referring now to FIG. 7, shown is one embodiment of an improved optical fiber adaptor 740. According to this embodiment, adaptor 740 is external to the laser system and is configured to connect into the fiber port through its proximal end and to accept an optical fiber at its distal end. According to another embodiment, adaptor 740 is internal to the laser system and its distal end functions as the fiber port of the laser system.

Adaptor 740 includes a tapered section 741 having a core area 710 and a clad area 711. Parallel section 742 has a structure which contains a core area 720 and a capillary 721 around it which is configured to act as a clad area. The refractive index of capillary 721 is higher than the refractive index of core area 710. As known to those skilled in the art, the NA of the assembly defined by core area 710 and capillary 721 is defined by $(n\_core^2 - n\_clad^2)^{0.5}$. The critical angle, $\alpha_c$, for the assembly of the core area 710 and capillary 721 is defined by $\arcsin(n\_clad/n\_core)$. Element 722 is a heat sink which is configured to absorb leaked optical energy from capillary 721. As described above, rays propagated through tapered section 741 double their incident angle each time they hit clad 711 before entering core section 720.

According to an aspect of the invention, rays propagating into core area 720 and characterized by incident angle greater than the critical angle $\alpha_c$ of the assembly, such as, for example, ray $R_2$ having an incident angle β when reaches core section 720, will leak from core area 720 into clad area 721 and will further be absorbed by heat sink 722. However, rays which enter core area 720 and are characterized by incident angles smaller than critical angle $\alpha_c$ of the assembly, such as, for example, ray $R_1$ having an incident angle α when reaches core section 720, will propagate along core 720 and into optical fiber 743. Therefore, according to another aspect of the invention, adaptor 740 is configured to propagate a laser beam from free space through its proximal end having a diameter D so as to deliver at least a portion of such laser beam into optical fiber having a diameter d in such a way that at least part of the beam rays which have an incident angle greater than the critical angle, $α_c$ of optical fiber 743 will be filtered out.

According to this aspect, only beam rays which are able to safely propagate along optical fiber 743 having incident angle smaller than $α_{c\_fiber}$ will be delivered into fiber 743. According to another aspect, the NA of parallel section 742 of adaptor 740 is about the same as the NA of fiber 743. According to another aspect, the NA of parallel section 742 is smaller or bigger than the NA of fiber 743.

According to another aspect of the invention, area 1210 represents an angled distal end portion of capillary 721 which tends to reflect internal reflections occurring within area 721 into the direction of the heat sink rather than into the core area 720. Such internal reflections inside capillary 721 may occur when rays, such as $R_2$, leave section 720 into heat sink 722.

Ferrule 744 is configured to establish a physical contact at the distal end of adaptor 740 with optical fiber 743. Ferrule 744 may be part of a fiber port which is configured, among other things, to mechanically align the distal end of core area 420 and the proximal end of optical fiber 743.

According to one embodiment, the proximal maximum diameter of tapered section 741, D, is in the range of 300μ to 600μ or in the range of 400μ to 500μ and the diameter of core 420 is in the range of 100μ to 600μ or in the range of 200μ to 400μ. According to one embodiment, adaptor 740 is configured to accept an incident laser beam at its proximal end which is characterized by a first numerical aperture and to emit at least part of the laser beam through its distal end which is characterized by a second numerical aperture. According to one embodiment, the first numerical aperture of the received laser beam is higher than the second numerical aperture of the laser beam exiting the distal end of optical fiber adaptor 740.

According to another embodiment, the first numerical aperture is about the same as the second numerical aperture. According to another aspect of the invention, adaptor 740 is configured to receive a first incident laser beam at its proximal end which is characterized by a first power and to emit a second laser beam from an aperture at its distal end which is characterized by a second power, wherein the first power is greater than the second power. A heat sink 722 located around clad area 721 is configured to accept, absorb and remove the heat due to such power differences.

According to yet another aspect of the invention, adaptor 740 is configured to couple optical fiber 743 at an aperture at its distal end. The aperture is configured to establish a physical contact between a proximal end of optical fiber 743 and the distal end of core area 720. Such a physical contact is configured to mechanically align the distal end of core 720 and the core material of optical fiber 743, which allows an optical coupling between the two elements.

According to another aspect of the invention, the diameter d of the optical fiber 743 may be at least ⅔ of the diameter D which characterizes the proximal end of adaptor 740. According to another embodiment, the diameter d of the optical fiber 743 may be at least ½ of the diameter D which characterizes the proximal end of adaptor 740.

Core area 710 of tapered section 41 may be welded or optically coupled to the core area 720 of parallel section 42. According to another embodiment, core area 710 of tapered section 741 and core area 720 of parallel section 742 may be made as single monolithic unit which is drawn together or manufactured as a single unit in any other way. Since adaptor 740 is an assembly separate from optical fiber 743, optical fiber 743 in use may be a simple optical fiber such as an optical fiber made of fused silica, while core elements 710 and 720 of the tapered and parallel sections respectively may be made of more expensive materials such as crystal silica, sapphire or germanium having superior optical behavior characteristics. Using a proper clad material 721, as known to those skilled in the art, the numerical aperture of the assemble 720-721 may be defined. The numerical aperture of the assembly may be higher, similar or lower than the numerical aperture of tapered section 741. The numerical aperture of the assembly may be higher, similar or lower than the numerical aperture of optical fiber 743.

What we claim is:

1. In an optical fiber assembly including a central optical fiber core having a longitudinal axis surrounded by a cladding layer along the longitudinal axis, a distal end portion and a proximal end portion;
   further comprising:
   a layer of a material at least partially surrounding the cladding layer;
   the layer of material being light-sensitive;
   and,
   at least two electrodes embedded at least partially along the longitudinal axis within the layer of light-sensitive material.

2. The optical fiber assembly of claim 1, wherein the light-sensitive material is a photoresist material.

3. The optical fiber assembly of claim 2, wherein the photoresist material characteristics change proportional to the amount of light impinging on the photoresist material.

4. The optical fiber assembly of claim 3, wherein the characteristics include one or more of electrical resistance changes or voltage changes.

5. The optical fiber assembly of claim 3, further comprising a console, the console including a laser source for producing laser light energy, and wherein the proximal end portion of the optical fiber assembly is received in the laser source.

6. The optical fiber assembly of claim 5, wherein the console includes a programmable controller, and wherein the controller is configured to activate the laser source, whereby activation of the laser source causes laser light energy to flow from the laser source to the proximal end portion of the central optical fiber core through to and out the distal end portion.

7. The optical fiber assembly of claim 5, wherein the at least two electrodes are operatively connected to the console, the console further comprising circuitry for imposing a voltage potential across the at least two electrodes, and wherein the console further comprises circuitry to detect a change in the voltage potential imposed and forward the detected change to the controller for display on the console.

8. The optical fiber assembly of claim 7, wherein the at least two electrodes are one of: mechanically or electronically connected to the console.

9. The optical fiber assembly of claim 7, wherein any laser light energy which passes through the cladding layer is received in the photoresist material and sensed by the at least two electrodes, the sensing causing a change in the imposed voltage potential across the at least two electrodes.

10. The optical fiber assembly of claim 9, wherein the controller is configured to receive the change in the imposed potential voltage detected by the detect circuitry, the controller providing one or more of a visual, auditory, numerical or graphical indication to a user of the change in imposed voltage potential on a user interface on the console.

11. The optical fiber assembly of claim 10, wherein a change in potential due to light energy leakage is caused by bending of the optical fiber core beyond a critical radius of curvature of the optical fiber core.

12. The optical fiber assembly of claim 11, wherein the controller provides one or more of a visual or numerical indication of bending beyond the critical radius.

13. The optical fiber assembly of claim 7, further comprising a temperature sensor mounted on the distal end portion of the optical fiber assembly.

14. The optical fiber assembly of claim 13, wherein the temperature sensor is operatively connected to one or more of the at least two electrodes, whereby changes in the temperature sensed by the temperature sensor are transmitted to the console for display of the sensed temperature on the console.

15. A method of detecting leakage of an optical fiber assembly, the optical fiber assembly including a central optical fiber core having a longitudinal axis surrounded by a cladding layer along the longitudinal axis, a distal end portion and a proximal end portion;
the assembly further including a layer of a material at least partially surrounding the cladding layer; the layer of material being light-sensitive; and, at least two electrodes embedded at least partially along the longitudinal axis within the layer of light-sensitive material, and a laser source for producing laser energy, the method comprising:
providing a voltage potential bias across the at least two electrodes;
providing a reading of the voltage potential bias in the absence of the laser source producing laser energy;
activating the laser source;
detecting a change in voltage potential bias across the at least two electrodes when the laser source is activated, whereby the change in voltage potential is a function of leakage of laser light energy through the cladding layer to the layer of light-sensitive material.

16. The method of claim 15, wherein the light-sensitive material is a photoresist.

17. The method of claim 15, wherein a change in voltage potential due to light energy leakage is caused by bending of the optical fiber core beyond a critical radius of curvature of the optical fiber core.

* * * * *